United States Patent
Kim et al.

(10) Patent No.: US 7,745,099 B2
(45) Date of Patent: Jun. 29, 2010

(54) PHOTOSENSITIVE COMPOUND AND PHOTORESIST COMPOSITION INCLUDING THE SAME

(75) Inventors: Jung-Woo Kim, Hwaseong-Si (KR); Deog-Bae Kim, Hwaseong-Si (KR); Jae-Hyun Kim, Seoul (KR)

(73) Assignee: Dongjin Semichem Co., Ltd., Incheon (KR)

( * ) Notice: Subject to any disclaimer, the term of this patent is extended or adjusted under 35 U.S.C. 154(b) by 0 days.

(21) Appl. No.: 12/270,532

(22) Filed: Nov. 13, 2008

(65) Prior Publication Data

US 2009/0246684 A1    Oct. 1, 2009

(30) Foreign Application Priority Data

Nov. 14, 2007    (KR) .................. 10-2007-0116187

(51) Int. Cl.
   *G03F 7/039*    (2006.01)
   *G03F 7/038*    (2006.01)
   *G03F 7/20*     (2006.01)
   *G03F 7/30*     (2006.01)
   *G03F 7/38*     (2006.01)

(52) U.S. Cl. .................. 430/270.1; 430/326; 430/325; 430/330; 560/59; 560/64; 560/73; 528/361

(58) Field of Classification Search ........................ None
See application file for complete search history.

(56) References Cited

OTHER PUBLICATIONS

Cho et al ("Supramolecular Nanostructures from Side Chain Rod-Coil Polymer Self-Assembly" Macromolecules, 2002, 35(12), p. 4845-4848.*

* cited by examiner

*Primary Examiner*—Sin J. Lee
(74) *Attorney, Agent, or Firm*—Birch, Stewart, Kolasch & Birch, LLP

(57) ABSTRACT

A photosensitive compound as a molecular resist whose size is smaller than conventional polymer for photoresist, and which can form a nano assembly, and a photoresist composition including the same are disclosed. The photosensitive compound represented by the following formula. Also, the present invention provides a photoresist composition comprising 1 to 85 wt % (weight %) of the photosensitive compound; 0.05 to 15 weight parts of a photo-acid generator with respect to 100 weight parts of the photosensitive compound; and 50 to 5000 weight parts of an organic solvent with respect to 100 weight parts of the photosensitive compound.

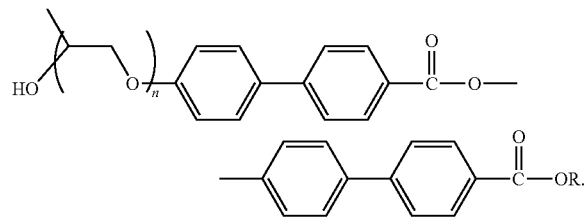

In the formula, n is the number of repetition of an isopropyl oxide (—CH(CH$_3$)CH$_2$O—) monomer, and is an integer of 1 to 40, and R is an alkyl group of 1 to 20 carbon atoms or a cycloalkyl group of 3 to 20 carbon atoms.

5 Claims, 1 Drawing Sheet

PHOTOSENSITIVE COMPOUND AND PHOTORESIST COMPOSITION INCLUDING THE SAME

This application claims the priority benefit of Korean Patent Application No. 10-2007-0116187 filed on Nov. 14, 2007. All disclosure of the Korean Patent application is incorporated herein by reference.

FIELD OF THE INVENTION

This invention relates to a photosensitive compound and a photoresist composition including the same, and more particularly to a photosensitive compound, as a molecular resist whose size is smaller than conventional polymer for photoresist, capable of forming a nano-assembly and a photoresist composition including the same.

BACKGROUNDS OF THE INVENTION

The photolithography is a process used to form a circuit pattern of a semiconductor chip or a display element from a semiconductor wafer or a glass for the display element. The photoresist composition is the most essential materials to the photolithography process. So recently, as the patterns for semiconductor devices and the display elements are finer, the need for the photoresist composition having high resolution is more increased.

Conventional acid-amplified photoresist composition includes a polymer resin, a photo-acid generator (PAG) and an organic solvent, and further includes a base compound as occasion demands. Since the conventional photoresist composition includes the polymer resin as a main component, it has excellent mechanical properties such as processibility, coating stability, etching resistance and can be easily removed after the succeeding process including an etching process, an ion implantation process and so on. However, it has a disadvantage in that the resolution of photoresist composition is restricted by the size of polymer resin. That is, in the photolithography process, it is impossible to form the pattern which has smaller size than the photosensitive polymer resin included in a photoresist composition. Also, as the structure of semiconductor changes to fine structure of 65 nm and below, the resist which has a polymer as main component cannot offer uniformity for fine patterns. This is because the polymer component composed of polymer chains with various structure, has randomicity to itself.

SUMMARY OF THE INVENTION

Therefore, it is an object of the present invention to provide a photosensitive compound which can be used as a molecular resist and has size smaller than conventional polymer for photoresist, and a photoresist composition including the same. It is another object of the present invention to provide a photosensitive compound which can improve layer-uniformity after coating or forming pattern as well as resolution of lithography process and line edge roughness (LER), and a photoresist composition including the same.

In order to achieve these objects, the present invention provides a photosensitive compound represented by the following Formula 1,

[Formula 1]

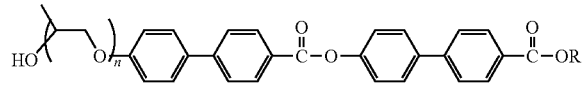

In the Formula 1, n is the number of repetition of an isopropyl oxide (—CH(CH$_3$)CH$_2$O—) monomer, and is an integer of 1 to 40, and R is an alkyl group of 1 to 20 carbon atoms or a cycloalkyl group of 3 to 20 carbon atoms.

The present invention also provides a photoresist composition comprising 1 to 85 wt % (weight %) of the photosensitive compound; 0.05 to 15 weight parts of a photo-acid generator with respect to 100 weight parts of the photosensitive compound; and 50 to 5000 weight parts of an organic solvent with respect to 100 weight parts of the photosensitive compound. Also, the present invention provides a method for forming photoresist pattern comprising the step of: (a) coating a photoresist composition on a substrate to form a photoresist layer; (b) exposing the photoresist layer to a light; (c) heating the exposed photoresist layer; and (d) developing the heated photoresist layer to form the photoresist pattern.

DETAILED DESCRIPTION OF THE INVENTION

A more complete appreciation of the invention, and many of the attendant advantages thereof, will be better appreciated by reference to the following detailed description.

The photosensitive compound according to the present invention has a structure which can be deprotected by an acid, and is represented by the following Formula 1.

[Formula 1]

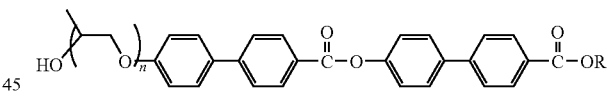

In the Formula 1, n is the number of repetition of an isopropyl oxide (—CH(CH$_3$)CH$_2$O—) monomer, and is an integer of 1 to 40, preferably 3 to 27. R is an acid sensitive protecting group, and is an alkyl group of 1 to 20 carbon atoms (C$_1$~C$_{20}$) or a cycloalkyl group of 3 to 20 carbon atoms. If necessary, the R can be substituted by one or more substituent selected from the group consisting of a hydroxyl group and a halogen group, and can comprise an ether group or an ester group. For example, R is an alkyl group or a cycloalkyl group of C$_5$~C$_{20}$ which comprise a hydroxyl group and/or a halogen group, or comprise an ether group or an ester group.

The representative examples of the photosensitive compound represented by the Formula 1 include compounds represented by the following Formulas 2a to 2g.

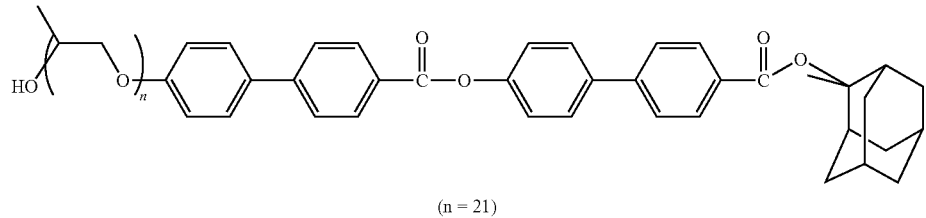
[Formula 2a]
(n = 21)
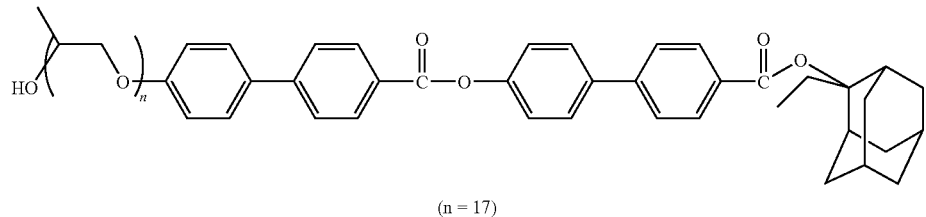
[Formula 2b]
(n = 17)
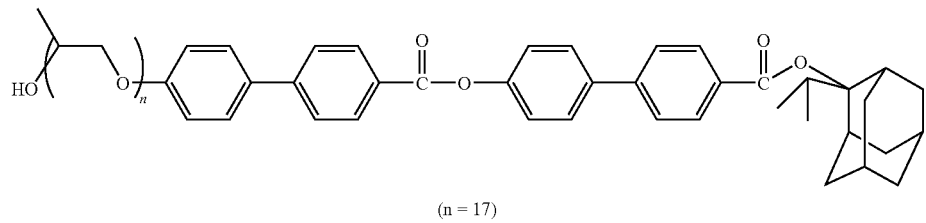
[Formula 2c]
(n = 17)
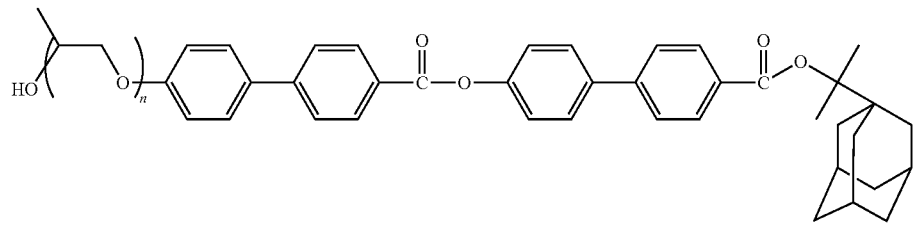
[Formula 2d]
(n = 13)
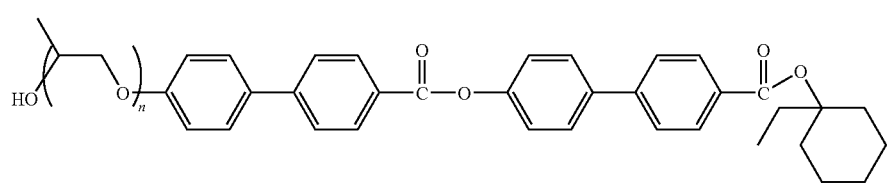
[Formula 2e]
(n = 21)
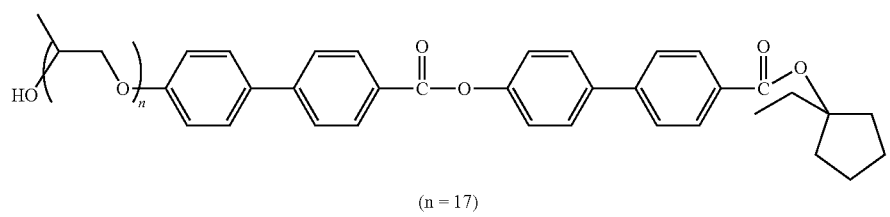
[Formula 2f]
(n = 17)

-continued

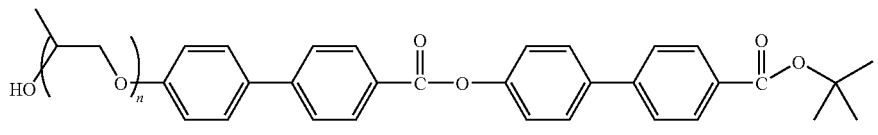
[Formula 2g]

(n = 21)

Figure 1:
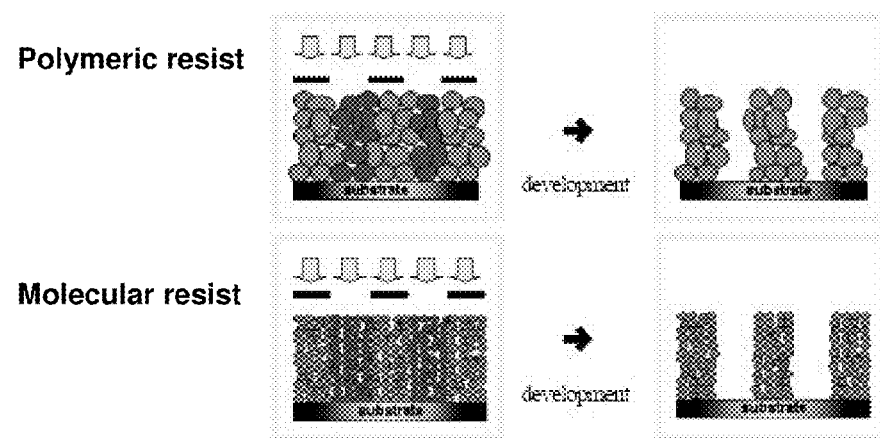
FIG. 1 shows the pattern forming process of polymeric resist and molecular resist.
Figure 2:
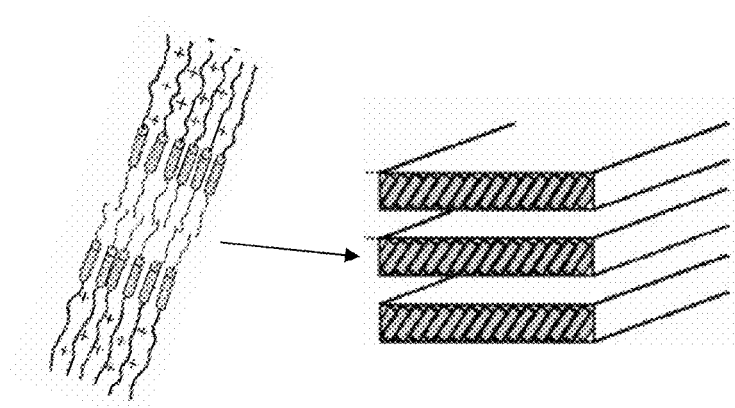
FIG. 2 shows the photosensitive compound accumulated in lamellar structure of block copolymer by controlling hydrophilic part and hydrophobic part of the photosensitive compound of the present invention.

Molecular self-assembly is a term used to describe processes in which a disordered system of pre-existing components forms an organized structure or pattern such as specified nano-structure by a covalent bond between atoms or an attraction between molecules, without external direction. One example of organized structures is a block copolymer. By applying the self-assembly to the present invention, hyperfine pattern which can not be formed easily by conventional lithography process, can be formed through processes of high sensitive nano-patterning and nano-imprint by extreme ultraviolet lithography (EUVL). The nano-imprint is one kind of process for creating layer patterns by stamp-like transferring the pattern on a substrate coated by thermoplastic resin or photo-curable resin. The line edge roughness (LER) can be effectively improved because the photosensitive compounds of the present invention are arranged regularly and protection groups are equally deprotected by the acid generated from exposure part. FIG. 1 is the figure showing the pattern forming process of polymeric resist and molecular resist. In the case of molecular resist (the lower figure of FIG. 1), the line edge roughness is good after developing, while in the case of polymeric resist (the upper figure of FIG. 1), the LER is poor after developing. Besides, in the photosensitive compound of the present invention, hydrophilicity and hydrophobicity can be controlled by changing the number of repetition of an isopropyl oxide (—CH(CH$_3$)CH$_2$O—) monomer. FIG. 2 shows that the photosensitive compound is accumulated in lamellar structure of block copolymer by controlling hydrophilic part and hydrophobic part of the photosensitive compound of the present invention. If using the photosensitive compound according to the present invention, only exposed region can be selectively developed because the protecting group (R) is deprotected by the acid generated by a photo-acid generator (PAG) under exposing process and solubility in developer is increased.

The photosensitive compound of the present invention can be synthesized by conventional organic synthetic methods. For example, the photosensitive compound represented by the Formula 1 is synthesized by an esterification reaction which is condensation between ester and carboxylic acid.

The photoresist composition according to the present invention includes the photosensitive compound represented by the Formula 1, a photo-acid generator and an organic solvent, and, if necessary, further includes a base compound as a quencher, and a surfactant. In the photoresist composition, the amount of the photosensitive compound is 1 to 85 wt % (weight %), preferably 1 to 45 wt %, more preferably 10 to 30 wt %, the amount of the photo-acid generator is 0.05 to 15 weight parts, preferably 0.15 to 5.5 weight parts with respect to 100 weight parts of the photosensitive compound, and the amount of the organic solvent is 50 to 5000 weight parts, preferably 200 to 500 weight parts with respect to 100 weight parts of the photosensitive compound. Also, the amount of the base compound, if used, is 0.01 to 10 weight parts, preferably 0.15 to 5 weight parts with respect to 100 weight parts of the photosensitive compound. Wherein, if the amount of the photosensitive polymer is too little (less than 1 wt %), it is difficult to form the photoresist layer with a desired thickness. If the amount of the photosensitive polymer is too much (more than 85 wt %), the thickness of patterns formed on the wafer may be not uniform. Also, if the amount of the photo-acid generator is too little (less than 0.05 weight parts), the light sensitivity of the photoresist composition may decrease. if the amount of the photo-acid generator is too much (more than 15 weight parts), the profile of the photoresist patterns may be deteriorated because the photo-acid generator absorbs a lot of ultraviolet rays and a large quantity of acid is produced from the photo-acid generator. Also, if the amount of the base compound is too little (less than 0.01 weight parts), it is not easy to control a diffusion of the acid generated in an exposure process so that the pattern profile is uneven. If the amount of the base compound is too much (more than 10 weight parts), the diffusion of the acid generated is suppressed so that pattern is not easily formed.

As the photo-acid generator, any conventional photo-acid generator which can generate an acid when exposed to a light, can be used. The non-limiting examples of the photo-acid generator include onium salts such as sulfonium salts or iodonium salts. Specifically, the photo-acid generator is selected from the group consisting of phthalimidotrifluoromethane sulfonate, dinitrobenzyltosylate, n-decyl disulfone and naphthylimido trifluoromethane sulfonate. Also, the photo-acid generator is selected from the group consisting of diphenyl iodonium triflate, diphenyl iodonium nonaflate, diphenyl iodonium hexafluorophosphate, diphenyl iodonium hexafluoroarsenate, diphenyl iodonium hexafluoroantimonate, diphenyl p-methoxyphenyl sulfonium triflate, diphenyl p-toluenyl sulfonium triflate, diphenyl p-tert-butylphenyl sulfonium triflate, diphenyl p-isobutylphenyl sulfonium triflate, triphenylsulfonium triflate, tris(p-tert-butylphenyl) sulfonium triflate, diphenyl p-methoxyphenyl sulfonium nonaflate, diphenyl p-toluenyl sulfonium nonaflate, diphenyl p-tert-butylphenyl sulfonium nonaflate, diphenyl p-isobutylphenyl sulfonium nonaflate, triphenylsulfonium nonaflate, tris(p-tert-butylphenyl) sulfonium nonaflate, triphenylsulfonium hexafluoroarsenate, triphenylsulfonium hexafluoroantimonate, triphenylsulfonium triflate and dibutylnaphtylsulfonium triflate.

As the organic solvent, the conventional various organic solvents for the photoresist composition can be used. Exemplary organic solvents include, but are not limited to, ethyleneglycol monomethylethyl, ethyleneglycol monoethylether, ethyleneglycol monomethylether, ethyleneglycol monoacetate, diethylene glycol, diethyleneglycol monoethylether, propyleneglycol monomethyletheracetate (PGMEA), propyleneglycol, propyleneglycol monoacetate, toluene, xylene, methylethylketone, methyl isoamyl ketone, cyclohexanone, dioxane, methyl lactate, ethyl lactate, methyl pyruvate, ethyl pyruvate, methyl methoxy propionate, ethyl ethoxy propionate, N,N-dimethylformamide, N,N-dimethylacetamide, N-methyl-2-pyrollidone, 3-ethoxy ethyl propionate, 2-heptanone, γ-butyrolactone, ethyl 2-hydroxy propionate, ethyl 2-hydroxy-2-methyl propionate, ethoxyethyl acetate, hydroxylethyl acetate, methyl 2-hydroxy-3-methylbutanoate, methyl 3-methoxy-2-methylpropionate, ethyl 3-ethoxy propionate, ethyl 3-methoxy-2-methyl propionate, ethyl acetate, butyl acetate, and mixture thereof.

Also, as the base compound which is used as quencher or reaction inhibitor, the conventional quenchers or reaction inhibitors, for example, organic bases such as tri-ethylamine, trioctylamine, tri-iso-butylamine, tri-iso-octylamine, di-ethanolamine, tri-ethanolamine and mixture thereof, can be used without limitation. The surfactant, at need, is added in the present photoresist composition so as to improve a mixing uniformity of the photoresist composition, coating property of the photoresist composition and developing property of the photoresist film after the light exposure. As the surfactant, conventional various surfactant as the photoresist composition can be used. Exemplary surfactants include, but are not limited to, fluorine-based surfactant or fluorine-silicon-based surfactant. The amount of the surfactant is 0.001 to 2 weight parts, preferably 0.01 to 1 weight parts with respect to solid content 100 weight parts of the photoresist composition. If the amount of the surfactant is too little, function of surfactant does not sufficiently work, and if the amount of the surfactant is too much, the resist property such as shape stability or a storage stability of the composition except for the coating property, may be adversely affected. Also, if necessary, as the photosensitive polymer according to the present invention, conventional photosensitive polymer for the photoresist, which reacts with an acid and its solubility to a developer is changed within the limits not to interfere the role of the light sensitive compound, can be used. The photosensitive polymer may be block copolymer or random copolymer having acid sensitive protecting group, and the weight average molecular weight (Mw) of photosensitive polymer is preferably 3,000 to 20,000.

In order to form a photoresist pattern with the photoresist composition according to the present invention, the following conventional photolithography process can be carried out. (i) First, the photoresist is applied or coated on a substrate such as silicon wafer, an aluminum substrate, and so on, for example, with a spin coater to form a photoresist layer. (ii) The photoresist layer is exposed to a light of a predetermined pattern. (iii) After the exposure, if necessary, the photoresist pattern is thermally treated(heated), which is called as PEB (Post Exposure Bake), and is developed to form the photoresist pattern. As the developing solution for the developing process, an alkali aqueous solution including an alkali compound such as sodium hydroxide, potassium hydroxide, sodium carbonate, tetramethylammonium hydroxide (TMAH) of the concentration of 0.1 to 10 weight % can be used. If necessary, the developing solution may further include water-soluble organic solvent such as methanol, ethanol, and a surfactant of a proper amount.

Hereinafter, the preferable examples are provided for better understanding of the present invention. However, the present invention is not limited by the following examples.

Examples 1-1 to 1-7

Preparation of Photosensitive Compound Represented by the Formula 2a to 2g

A. Preparation of Compounds 1-1 to 1-7

As shown in the following Reaction 1 and Table 1, under nitrogen atmosphere, polypropylene glycol (wherein, n is the number of repetition of an isopropyl oxide (—CH(CH$_3$)CH$_2$O—) monomer) and toluenesulfonyl chloride are dissolved in methylene chloride, and reacted for 12 hours with pyridine (6.27 ml, 77.6 mmol) which is added at room temperature. After completion of the reaction, reaction solution is washed by water, and extracted and separated by methylene chloride and then filtered through anhydrous magnesium sulfate. After evaporating methylene chloride from the remained solution by using vacuum distiller, colorless liquid compounds 1-1 to 1-7 are obtained by column chromatography using silica gel. The yields thereof are listed in Table 1.

TABLE 1

[Reaction 1]

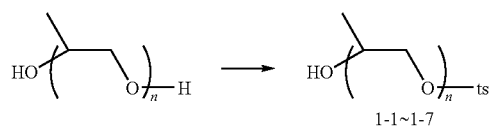

1-1~1-7

(Wherein, ts is a toluenesulfonyl group)

|  | The number of repetition of an isopropyl oxide monomer (n) | The amount of propylene glycol | The amount of toluenesulfonyl chloride | Yield (%) |
| --- | --- | --- | --- | --- |
| compound 1-1 | 21 | 50 g (40.5 mmol) | 20 g (104.9 mmol) | 77.0% |
| compound 1-2 | 17 | 50 g (49.8 mmol) | 20 g (104.9 mmol) | 80.7% |
| compound 1-3 | 17 | 50 g (49.8 mmol) | 20 g (104.9 mmol) | 76.7% |
| compound 1-4 | 13 | 50 g (64.8 mmol) | 20 g (104.9 mmol) | 71.6% |
| compound 1-5 | 21 | 50 g (40.5 mmol) | 20 g (104.9 mmol) | 72.8% |
| compound 1-6 | 17 | 50 g (49.8 mmol) | 20 g (104.9 mmol) | 80.6% |
| compound 1-7 | 21 | 50 g (40.5 mmol) | 20 g (104.9 mmol) | 84.2% |

B. Preparation of Compounds 2-1 to 2-7

As shown in the following Reaction 2, compounds 1-1 to 1-7 and ethyl-4-hydroxy-4-biphenylcarboxylate are dissolved in ethanol (EtOH), and reacted with reflux at 80° C. for 12 hours with potassium carbonate. After the completion of the reaction, the reaction solution is stirred at room temperature for 3 hours with excess potassium hydroxide. Reaction solution is washed by water, and extracted and separated by methylene chloride, and then filtered through anhydrous magnesium sulfate. After evaporating methylene chloride from the remained solution by vacuum distiller, colorless liquid compounds 2-1 to 2-7 are obtained by column chromatography using silica gel.

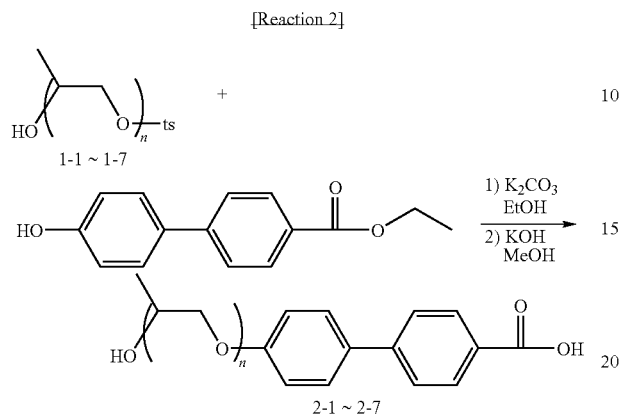

C. Preparation of Compounds 3-1 to 3-3

As shown in the following Reaction 3 and Table 2, 4-hydroxy-4'-biphenylcarboxylic acid and R—Br (Wherein,

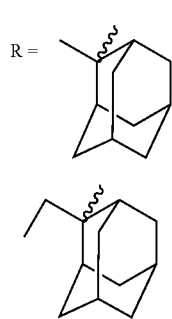

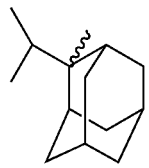

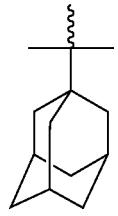

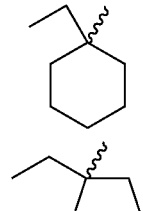

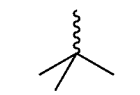

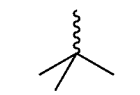

and broken lines indicate bonding parts. If R is 2a, R—Br is 2-methyl-2-adamantyl bromide) are dissolved in the mixed solvent of acetone 20 ml and dimethyl sulfoxide (DMSO) 20 ml, and reacted with reflux at 60° C. for 36 hours with potassium carbonate. Reaction solution is extracted and separated by water, hydrochloric acid and methylene chloride, and then filtered through anhydrous magnesium sulfate. After evaporating methylene chloride from the remained solution by vacuum distiller, white solid compounds 3-1 to 3-7 are obtained by recrystallization using methanol and hexane. The yields thereof are listed in Table 2.

TABLE 2

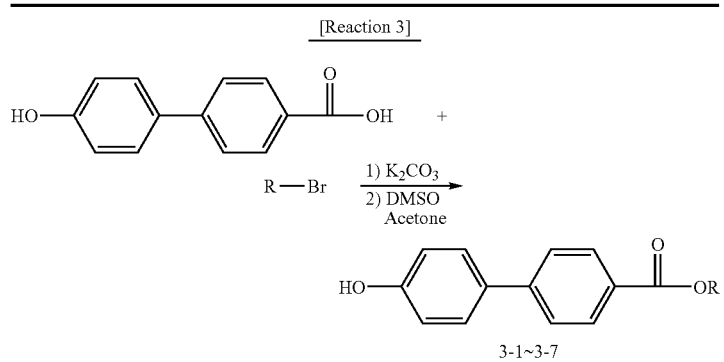

| | R—Br (R = 2a to 2g) | 4-hydroxy-4'-biphenylcarboxylic acid | Yield (%) |
|---|---|---|---|
| compound 3-1 | 16.0 g (69.8 mmol) | 3.0 g (14.0 mmol) | 36.4% |
| compound 3-2 | 16.0 g (66.1 mmol) | 3.0 g (14.0 mmol) | 31.8% |
| compound 3-3 | 16.0 g (62.5 mmol) | 3.0 g (14.0 mmol) | 40.9% |
| compound 3-4 | 16.0 g (62.2 mmol) | 3.0 g (14.0 mmol) | 37.2% |
| compound 3-5 | 16.0 g (83.7 mmol) | 3.0 g (14.0 mmol) | 41.6% |
| compound 3-6 | 16.0 g (90.4 mmol) | 3.0 g (14.0 mmol) | 39.5% |
| compound 3-7 | 16.0 g (116.7 mmol) | 3.0 g (14.0 mmol) | 40.1% |

D. Preparation of Compounds Represented by the Formula 2a to 2g

As shown in the following Table 3, under nitrogen atmosphere, compounds 2-1 to 2-7, compounds 3-1 to 3-7 and 4-(Dimethylamino)pyridinium 4-toluenesulfonate (DPTS, 0.63 g 2.1 mmol) are methylene chloride 100 ml, and reacted at room temperature for 24 hours with 1,3-diisopropyl carbodiimide (DIPC). After the completion of the reaction, reaction solution is washed by water, and extracted and separated by methylene chloride, and then filtered through anhydrous magnesium sulfate. After evaporating methylene chloride from the remained solution by vacuum distiller, white solid compounds represented by the Formula 2a to 2g are obtained by column chromatography using silica gel.

TABLE 3

| compound | The amount of compounds 2-1~2-7 | The amount of compounds 3-1~3-7 | Yield (%) |
|---|---|---|---|
| Formula 2a | 10.0 g (6.98 mmol) | 5.06 g (13.96 mmol) | 42.6% |
| Formula 2b | 10.0 g (8.32 mmol) | 6.24 g (16.64 mmol) | 45.8% |
| Formula 2c | 10.0 g (8.32 mmol) | 6.47 g (16.64 mmol) | 48.1% |
| Formula 2d | 10.0 g (10.3 mmol) | 8.04 g (14.0 mmol) | 41.6% |
| Formula 2e | 10.0 g (6.98 mmol) | 4.52 g (13.96 mmol) | 39.4% |
| Formula 2f | 10.0 g (8.32 mmol) | 5.16 g (16.64 mmol) | 42.7% |
| Formula 2g | 10.0 g (6.98 mmol) | 3.77 g (13.96 mmol) | 43.5% |

$^1$H-NMR data of the obtained compounds are as follows.

Compound represented by the Formula 2a $^1$H-NMR (CDCl$_3$, internal standard): δ (ppm) 8.20 (CH, 2H), 8.05 (CH, 2H), 7.63 (CH, 2H), 7.59 (CH, 2H), 7.55 (CH, 2H), 7.41 (CH, 2H), 7.25 (CH, 2H), 7.21 (CH, 2H), 3.72 (CH, 21H), 3.52 (CH$_2$, 42H), 2.0 (OH, 1H), 1.97 (H, 1H), 1.90 (H, 1H), 1.56 (H, 1H), 1.52 (H, 1H), 1.50 (CH3, 3H), 1.45 (H, 1H), 1.40 (H, 1H), 1.36 (CH$_2$, 2H), 1.21 (CH$_3$, 63H), 1.45 (CH$_2$, 2H), 1.36 (CH$_2$, 2H), 1.18 (H, 1H), 1.14 (H, 1H), 0.93 (H, 1H)

Compound represented by the Formula 2b $^1$H-NMR (CDCl$_3$, internal standard): δ (ppm) 8.20 (CH, 2H), 8.05 (CH, 2H), 7.63 (CH, 2H), 7.59 (CH, 2H), 7.55 (CH, 2H), 7.41 (CH, 2H), 7.25 (CH, 2H), 7.21 (CH, 2H), 3.72 (CH, 17H), 3.52 (CH$_2$, 34H), 2.29 (CH$_2$, 2H), 2.0 (OH, 1H), 1.97 (H, 1H), 1.90 (H, 1H), 1.56 (H, 1H), 1.52 (H, 1H), 1.45 (H, 1H), 1.40 (H, 1H), 1.36 (CH$_2$, 2H), 1.21 (CH$_3$, 51H), 1.45 (CH$_2$, 2H), 1.36 (CH$_2$, 2H), 1.18 (H, 1H), 1.14 (H, 1H), 0.93 (H, 1H), 0.90 (CH$_3$, 3H)

Compound represented by the Formula 2c $^1$H-NMR (CDCl$_3$, internal standard): δ (ppm) 8.20 (CH, 2H), 8.05 (CH, 2H), 7.63 (CH, 2H), 7.59 (CH, 2H), 7.55 (CH, 2H), 7.41 (CH, 2H), 7.25 (CH, 2H), 7.21 (CH, 2H), 3.72 (CH, 17H), 3.52 (CH$_2$, 34H), 2.41 (CH, 1H), 2.0 (OH, 1H), 1.97 (H, 1H), 1.90 (H, 1H), 1.56 (H, 1H), 1.52 (H, 1H), 1.45 (H, 1H), 1.40 (H, 1H), 1.36 (CH$_2$, 2H), 1.21 (CH$_3$, 51H), 1.45 (CH$_2$, 2H), 1.36 (CH$_2$, 2H), 1.18 (H, 1H), 1.14 (H, 1H), 1.01 (CH$_3$, 6H), 0.93 (H, 1H)

Compound represented by the Formula 2d $^1$H-NMR (CDCl$_3$, internal standard): δ (ppm) 8.20 (CH, 2H), 8.05 (CH, 2H), 7.63 (CH, 2H), 7.59 (CH, 2H), 7.55 (CH, 2H), 7.41 (CH, 2H), 7.25 (CH, 2H), 7.21 (CH, 2H), 3.72 (CH, 13H), 3.52 (CH$_2$, 26H), 2.0 (OH, 1H), 1.97 (H, 1H), 1.90 (H, 1H), 1.56 (H, 1H), 1.52 (H, 1H), 1.50 (CH$_3$, 3H), 1.45 (H, 1H), 1.40 (H, 1H), 1.36 (CH$_2$, 2H), 1.21 (CH$_3$, 39H), 1.45 (CH$_3$, 6H), 1.36 (CH$_2$, 2H), 1.18 (H, 1H), 1.14 (H, 1H), 1.11 (CH, 1H), 0.93 (H, 1H)

Compound represented by the Formula 2e $^1$H-NMR (CDCl$_3$, internal standard): δ (ppm) 8.20 (CH, 2H), 8.05 (CH, 2H), 7.63 (CH, 2H), 7.59 (CH, 2H), 7.55 (CH, 2H), 7.41 (CH, 2H), 7.25 (CH, 2H), 7.21 (CH, 2H), 3.72 (CH, 21H), 3.52 (CH$_2$, 42H), 2.0 (OH, 1H), 1.97 (H, 1H), 1.90 (H, 1H), 1.82 (CH$_2$, 4H), 1.71 (CH$_2$, 2H), 1.44 (CH$_2$, 6H), 1.21 (CH$_3$, 63H), 1.18 (H, 1H), 1.14 (H, 1H), 0.96 (CH$_3$, 3H)

Compound represented by the Formula 2f $^1$H-NMR (CDCl$_3$, internal standard): δ (ppm) 8.20 (CH, 2H), 8.05 (CH, 2H), 7.63 (CH, 2H), 7.59 (CH, 2H), 7.55 (CH, 2H), 7.41 (CH, 2H), 7.25 (CH, 2H), 7.21 (CH, 2H), 3.72 (CH, 17H), 3.52 (CH$_2$, 34H), 2.0 (OH, 1H), 1.97 (H, 1H), 1.90 (H, 1H), 1.89 (CH$_2$, 4H), 1.71 (CH$_2$, 2H), 1.51 (CH$_2$, 4H), 1.21 (CH$_3$, 51H), 1.18 (H, 1H), 1.14 (H, 1H), 0.96 (CH$_3$, 3H)

Compound represented by the Formula 2g $^1$H-NMR (CDCl$_3$, internal standard): δ (ppm) 8.20 (CH, 2H), 8.05 (CH, 2H), 7.63 (CH, 2H), 7.59 (CH, 2H), 7.55 (CH, 2H), 7.41 (CH, 2H), 7.25 (CH, 2H), 7.21 (CH, 2H), 3.72 (CH, 21H), 3.52 (CH$_2$, 42H), 2.0 (OH, 1H), 1.97 (H, 1H), 1.90 (H, 1H), 1.40 (CH$_3$, 9H), 1.21 (CH$_3$, 63H), 1.18 (H, 1H), 1.14 (H, 1H)

Examples 2-1 to 2-7

Preparation of Photoresist Composition and Formation of Photoresist Pattern Using the Photoresist Composition 2.0 g of each molecular resist photosensitive compound (compound of Formula 2a~2g) synthesized in the Example 1-1 to 1-7, 0.08 g of triphenylsulfonium triflate as an photoacid generator, 0.02 g of triethanolamine as a reaction inhibitor, and 20 g of propyleneglycol monomethyletheracetate (PGMEA) as an organic solvent are mixed and filtrated to prepare photoresist compositions. The prepared photoresist composition is spin-coated upon etching layer of silicon wafer to form a photoresist thin film. Then the photoresist thin film is prebaked at 130° C. for 90 seconds and then exposed by ArF ASML 1250 instrument whose Numerical Aperture is 0.85. Thereafter, the photoresist thin film is baked again (PEB, Post exposure bake) at 125° C. for 90 seconds. The baked wafer was dipped in 2.38 wt % trimethyl ammonium hydroxide (TMAH) aqueous solution for 30 seconds for developing to form 65 nm 1:1 line and space (L/S: line/space) pattern. The ability of the photoresist pattern (L/S pattern) is evaluated, and listed in the following Table 4. In the following Table 4, depth of focus (μm) is process margin, and is defined as the depth of exposure light to a resist layer. EOP is the most suitable amount of exposure light (mJ/cm$^2$), and is the suitable amount of exposure light for obtaining wanted pattern size. Receding angle (degree(°)) indicates the degree of hydrophobicity of photoresist.

TABLE 4

| Example | Minimum resolution [nm] | Depth of focus [um] | EOP [mJ/cm$^2$] | Line edge roughness [nm] | Receding angle (Degree, °) |
|---|---|---|---|---|---|
| Example 2-1 | 62 | 0.6 | 30 | 3.1 | 48 |
| Example 2-2 | 65 | 0.62 | 31 | 3.5 | 51 |
| Example 2-3 | 61 | 0.59 | 35 | 2.9 | 53 |
| Example 2-4 | 63 | 0.65 | 38 | 3.6 | 62 |
| Example 2-5 | 60 | 0.69 | 31 | 3.7 | 49 |
| Example 2-6 | 64 | 0.6 | 29 | 3.6 | 53 |
| Example 2-7 | 65 | 0.61 | 41 | 3 | 49 |

As shown in the Table 4, resolving power under 65 nm can be obtained in the case of patterning process using molecular resist composition according to the present invention and mask of 65 nm resolution (Examples 2-1 to 2-7), and the line edge roughness is remarkably improved by 2.9 to 3.7 nm in the case of using the composition according to the present invention while the line edge roughness is 5 to 6 nm in the case of using the conventional composition. Moreover, it can be confirmed that the value of receding angle of photoresist composition is changed by the number of repetition of an isopropyl oxide (—CH(CH$_3$)CH2O—) monomer, by measuring receding angle to check the hydrophilicity and the hydrophobicity of the resist compound. Besides, the pattern having lines and spaces of same width of 30 nm is successfully formed using the photoresist composition of the present invention, as the result of exposure with adjusting mask and wafer using the extreme ultraviolet exposure instrument.

The photosensitive compound of the present invention can use as a molecular resist whose size is smaller than conventional polymer for photoresist. Also, the photosensitive compound of the present invention can improve resolution of lithography process, and has advanced line edge roughness (LER), and can improve uniformity of layer after coating or forming pattern.

The invention claimed is:

1. A photosensitive compound which has a structure of the following Formula 1,

[Formula 1]

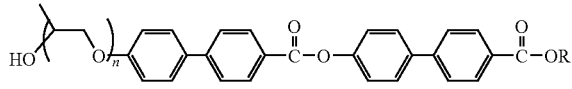

wherein in Formula 1, n is the number of repetition of an isopropyl oxide (—CH(CH$_3$)CH$_2$O—) monomer, and is an integer of 1 to 40, and R is an alkyl group or a cycloalkyl group of C$_5$~C$_{20}$ which comprises one or more substituents selected from the group consisting of a hydroxyl group and a halogen group, or comprises an ether group or an ester group.

2. A photosensitive compound, wherein the photosensitive compound is selected from the group consisting of compounds represented by the following Formulas, (n=21)

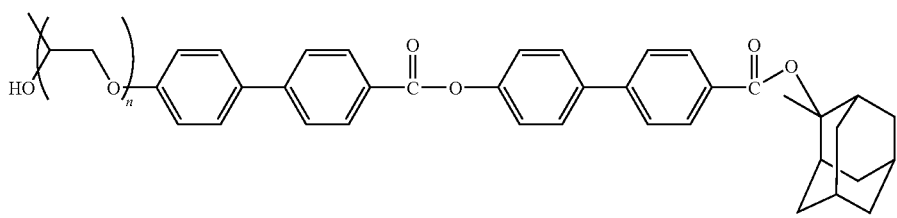

(n=17)

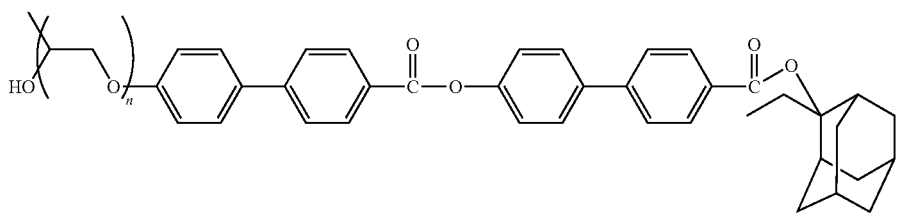

(n=17)

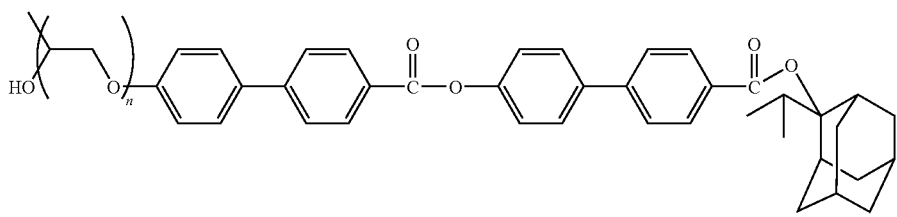

(n=13)

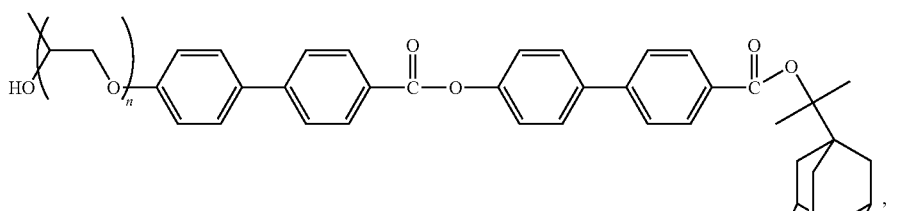

(n=21)

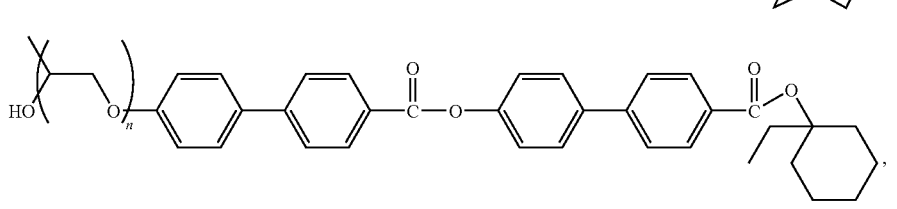

-continued

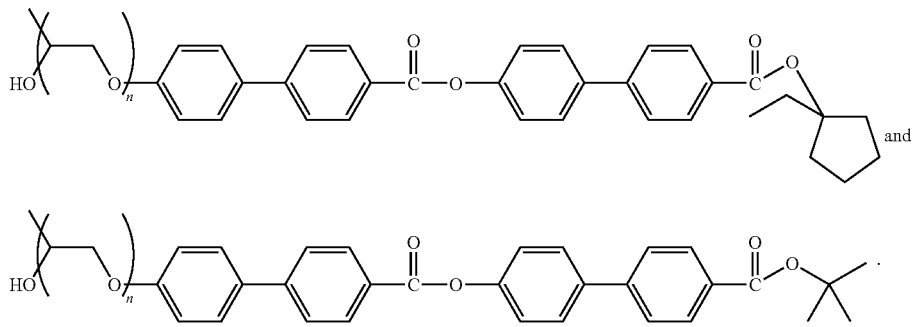

3. A photoresist composition comprising: 1 to 85 wt % of a photosensitive compound having a structure of the following Formula 1,

[Formula 1]

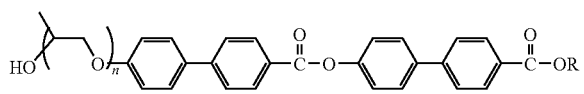

wherein, n is the number of repetition of an isopropyl oxide (—CH(CH₃)CH₂O—) monomer, and is an integer of 1 to 40, and R is an alkyl group of 1 to 20 carbon atoms or a cycloalkyl group of 3 to 20 carbon atoms;

0.05 to 15 weight parts of a photo-acid generator with respect to 100 weight parts of the photosensitive compound; and 50 to 5000 weight parts of an organic solvent with respect to 100 weight parts of the photosensitive compound.

4. The photoresist composition of claim 3, further comprising 0.01 to 10 weight parts of a base compound with respect to 100 weight parts of the photosensitive compound, wherein, the base compound is selected from a group of consisting of tri-ethylamine, tri-iso-butylamine, tri-iso-octylamine, di-ethanolamine, tri-ethanolamine and mixture thereof.

5. A method for forming a photoresist pattern, comprising the step of:
   a) coating a photoresist composition on a substrate to form a photoresist layer;
   b) exposing the photoresist layer to a light;
   c) heating the exposed photoresist layer; and
   d) developing the heated photoresist layer to form the photoresist pattern, wherein the photoresist composition comprises 1 to 85 wt % of a photosensitive compound having a structure of the following Formula 1,

[Formula 1]

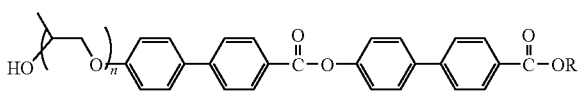

wherein, n is the number of repetition of an isopropyl oxide (—CH(CH₃)CH₂O—) monomer, and is an integer of 1 to 40, and R is an alkyl group of 1 to 20 carbon atoms or a cycloalkyl group of 3 to 20 carbon atoms;

0.05 to 15 weight parts of a photo-acid generator with respect to 100 weight parts of the photosensitive compound; and 50 to 5000 weight parts of an organic solvent with respect to 100 weight parts of the photosensitive compound.

* * * * *